United States Patent [19]

Dahmen et al.

[11] Patent Number: 4,644,083

[45] Date of Patent: Feb. 17, 1987

[54] PROCESS FOR THE PRODUCTION OF N-SUBSTITUTED α,β-UNSATURATED CARBOXYLIC ACID AMIDES

[75] Inventors: Kurt Dahmen, Monchen-Gladbach; Erich Küster, Krefeld; Richard Mertens, Krefeld; Helmut Brehm, Krefeld, all of Fed. Rep. of Germany

[73] Assignee: Chemische Fabrik Stockhausen GmbH, Krefeld, Fed. Rep. of Germany

[21] Appl. No.: 695,125

[22] Filed: Jan. 25, 1985

[30] Foreign Application Priority Data

Jan. 26, 1984 [DE] Fed. Rep. of Germany ....... 3402599

[51] Int. Cl.$^4$ ............... C07C 103/133; C07D 265/30; C07D 241/04; C07D 295/00
[52] U.S. Cl. .................................. 564/205; 564/204; 544/176; 544/399; 544/400
[58] Field of Search ............... 564/205, 204; 544/176, 544/399, 400

[56] References Cited

U.S. PATENT DOCUMENTS

4,228,102 10/1980 Besecke et al. ................. 564/204 X
4,288,390 9/1981 McDonald ........................... 564/204
4,408,073 10/1983 Goossens et al. ................... 564/204

*Primary Examiner*—Paul F. Shaver
*Attorney, Agent, or Firm*—Spring, Horn, Kramer & Woods

[57] ABSTRACT

The present invention relates to a process for the production of N-substituted α,β-unsaturated carboxylic acid amides, which proceeds from the α,β-unsaturated carboxylic acid amide that is unsubstituted at the amido nitrogen, which forms the Michael adduct initially by conversion with a polyvalent alcohol having a boiling point of $>/=150°$ C., converts this with a primary or secondary amine with elimination of ammonia to form N-substituted carboxylic acid amide with a protected double bond, the polyvalent alcohol being subsequently eliminated from this product at high temperatures, with formation of the N-substituted α,β-unsaturated carboxylic acid amide.

16 Claims, No Drawings

PROCESS FOR THE PRODUCTION OF N-SUBSTITUTED α,β-UNSATURATED CARBOXYLIC ACID AMIDES

The present invention relates to a process for the production of N-substituted α,β-unsaturated carboxylic acid amides in which the appropriate α,β-unsaturated carboxylic acid amide, unsubstituted at the amido nitrogen, is used.

N-substituted α,β-unsaturated carboxylic acid amides play an important role in many areas of technology. Representatives of this class of material are found, for example, among the monomers that are so significant in the plastics industry. N-substituted α,β-unsaturated carboxylic acid amides are also found in herbicides.

Synthesis processes, which permit a technically and economically satisfactory access to N-substituted α,β-unsaturated carboxylic acid amides have for this reason been the object of chemical research and development for a considerable time. However, up to the present it has proved impossible to gain complete access to N-substituted α,β-unsaturated carboxylic acid amides which entails no disadvantages.

A very thorough assessment of the advantages and disadvantages of synthesis processes that have been known for a considerable time is to be found in European patent specification No. 0 013 416.

In the best processes, known up to now, proceeding from α,β-unsaturated carboxylic acid esters or nitriles, the reactive double bond is protected by the addition of water, alcohols, or amines (the so-called Michael addition, for example, see O. Bayer, *Angew. Chem* [Applied Chemistry], 61 (1949), p. 229; *Org. React.* [Organic Reactions], 10 (1959), (p. 179). These protective groups are then split off after one or more reaction stages, with the reformation of the double bond. The splitting off reaction can be effected thermally, if necessary with the addition of catalysts.

A reaction series of this kind, which, it is true, proceeds from the acrylamide which is easily accessible in the gross technical sense, is described in European patent No. 0 070 425. In a single-stage reaction primary or secondary amine is added to the carbon double bond and subsequently transaminated with an excess of amine (analogously to corresponding processes with β-hydroxy or β-alkoxypropionamides, if the double bond is protected by water or an alcanol), with separation of ammonia, and then the amino protective group is once again split off during a further temperature increase in a vacuum, this resulting in the desired N-substituted acrylamide. A disadvantage of this multistage reaction is the fact—as the examples show—that the amine components have to be used in excess (approximately threefold). However, these amine components involve relatively costly compounds, particularly if the N-substituted α,β-unsaturated carboxylic acid amides that are particularly interesting, are to be produced. Such is the case, for example, with 3-dimethlyaminopropylamine and N',N'-3,3-tetramethylpropanediamine-1.3. In cases such as these, use of the process is linked with economic disadvantages that should not be disregarded, especially since the immediate re-use of the amine is linked with difficulties in view of the secondary reactions that can occur at the increased temperatures (200°–300° C.) involved in the final stage of the reaction (Hofmann and Cope elimination).

DE-OS Nos. 26 23 838 and 28 36 520 describe the production of N-substituted β-alkoxypropionamides and their decomposition to N-substituted (meth)acrylamides.

If short-chain alcohols are used as the protective group the N-substituted β-alkoxypropionamide can only be distilled when not decomposed, in contradiction to the lessons of DE-OS No. 26 23 838. Significant separation occurs only at higher temperatures. Governed by the high pyrolysis temperatures the formation of the secondary products is promoted and the yield of the product correspondingly reduced.

DE-OS No. 28 36 520 describes the use of basic catalysts in the pyrolysis stage, by which means the pyrolysis temperature can be reduced to approximately 100° C. Despite this, this process entails certain disadvantages. The basic catalysts initiate anionic secondary reactions—especially in the case of acrylamide derivatives, anionic condensation or polymeristion occur—and thereby cause undesirable loss of yield.

In the case of the Michael addition to the N-substituted α,β-unsaturated carboxylic acid amides attempts to use long-chain alcohols such as hexanol as the protective group lead only to low conversion. With the suitable addition of the α,β-unsaturated carboxylic acid ester, additional transesterisation results in a mixture of at least four products, and this results in considerable separation problems in the further conduct of the reaction.

Thus it is the task of the present invention to create a process that makes it possible to obtain N-substituted α,β-unsaturated carboxylic acid amides without any troublesome secondary reactions, by exploiting the protective effect of alcohols for carbon double bonds by transamidation and susequent pyrolysis. To this end it is essential that the alcoholic protective group can be converted easily and completely with the N-substituted α,β-unsaturated carboxylic acid amides and then separated off after transamidation without catalysts and at the lowest possible temperatures with the formation of the desired N-substituted carboxylic acid amides.

According to the present invention, this task has been solved in that the N-substituted α,β-unsaturated carboxylic acid amide that is unsaturated at the amide nitrogen is converted during base catalysis after the Michael reaction with an organic polyhydroxy compound containing at least two alcoholic OH-groups, with a boiling point of >/=150° C. at 1010 hPa, the resulting Michael adduct being converted with a primary or secondary amine with elimination of the ammonia to form N-substituted carboxylic acid amide with a protected double bond, the polyhydroxy compound being eliminated from this product at increased temperature, during formation of the N-substituted α,β-unsaturated carboxylic acid amide.

Surprisingly, it has been found that polyvalent alcohols with a boiling point of >/=150° C. at 1010 hPa (760 Torr) can be added easily to unsubstituted α,β-unsaturated carboxylic acid amides such as (meth)acrylamide and can be easily and completely separated off. The base catalysed addition of these polyhydroxy compounds to the unsubstituted α,β-unsaturated carboxylic acid amide that is unsubstituted at the amino nitrogen proceeds rapidly and completely without any notable secondary reactions, and the same applies to the re-separation.

Aliphatic polyvalent alcohols that can be straight or branched are particularly suitable as the polyhydroxy compounds that must contain at least two alcoholic OH-groups. Preferred are aliphatic diols with 2–6 carbon atoms, for example, 1,2-ethandiol. Equally suitable are the aliphatic triols with 3–6 carbon atoms, for example, glycerine or trimethylol propane. Even such polyvalent alcohols that contain hetero-atoms, such as aminoalcohols or at least bivalent alcohols that contain ether bridges are suitable. Examples of aminoalcohols are triethanol amine. Examples of ether alcohols are di-hydroxyether, especially di-(2)hydroxyethylether.

The addition of the polyhydroxy compounds, as a rule slightly exothermic, to the carboxylic acid amide is best carried out at a temperature of up to at least the boiling point of the polyhydroxy compound, preferably in the range of 20 to 70, particularly from 40°–50° C., in which connection the mol ratio of polyhydroxy compound and $\alpha,\beta$-unsaturated starting carboxylic acid amide is 0.75:1 to 2:1. It is preferred that equimolar quantities be used.

The Michael addition proceeds during basic catalysis with alkali hydroxides or alkali alcholates. Quarternary ammonium hydroxide such as benzyltrimethyl ammonium hydroxide (Triton B) as well as basis ion exchangers are also suitable as catalysts. The conversion takes place practically quantitatively. An addition of polymerisation inhibitor is possible, but not, as a rule, absolutely essential.

As a matter of principle, all $\alpha,\beta$-unsaturated compounds are suitable as starting carboxylic acid amides. Particularly preferred are carboxylic acid amides of the general formula

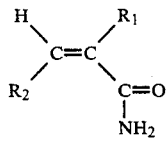

wherein $R_1$ and $R_2$ stand for hydrogen or methyl; typical examples are acrylamide, methacrylamide, and crotonamide.

The Michael adduct is best not isolated, but rather immediately transamidated with a primary or secondary, prerably aliphatic, amine.

In principle, all primary and secondary amines are suitable for the process according to the present invention; preferred are amines of the general formula

wherein either $R_3$ stands for hydrogen and $R_4$ stands for the radical $Q-R_5$, Q standing for an organic radical having 2 to 18 C atoms, straight or branched, substituted if necessary, or consisting of 5–6 element iso- or heterocyclic rings, preferably with nitrogen- and/or oxygen atoms as ring elements or containing such rings, or $R_3$ and $R_4$ stand in each instance for an alkyl radical with 1–5 carbon atoms, in which regard $R_3$ and $R_4$ can together also form a 5 or 6 element iso- or heterocyclic ring, $R_5$ standing for hydrogen, a dialkylamino group or alkoxy group, the alkyl of which in each instance contains 1–4 carbon atoms.

Typical representatives of amines that come under the general formula $HNR_3R_4$ are included in the general formulae

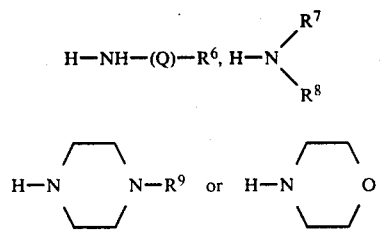

wherein Q has the same value as above, $R_6$, like $R_5$, $R_7$, and $R_8$, have the same value as $R_3$ and $R_4$ and $R_9$ stands for an alkyl radical with 1–4 carbon atoms.

Suitable are primary amines, such as methylamine, ethylamine, n-butylamine, 2-ethylhexylamine, cyclohexylamine methoxypropylamine, preferably N,N-dimethyl- and N,N-2,2-tetramethylpropanediamine-1,3 as well as N,N-dimethyl ethane diamine-1,2; of the secondary amines, dimethlyamine, dibutylamine, morpholine and N-methyliperazine are quoted as representatives. The transamidation, which takes place preferably, as has been mentioned, in the same vessel as the Michael addition, is preferably conducted in the presence of catalytic quantities—as a rule 1 to 5 mol %—of a carboxylic acid such as formic, acetic, propionic acid or butyric acid. These acids also serve to neutralize the basic catalyst of the Michael addition. Preferably, acrylic acid is used. Inorganic acids are, in principle, suitable as catalysts; however, as a rule they lead to difficulties in the subsequent pyrolysis.

In the transamidation the primary or secondary amine is as a rule used in a molar ratio of 1:1 to 1.5:1 relative to the $\alpha,\beta$-unsaturated carboxylic acid amide that is unsubstituted at the amide nitrogen. The yields from this reaction are as a rule higher than 90% of the theoretical. Any possible excess of the primary or secondary amine can be distilled off prior to pyrolysis. In order to avoid secondary reactions that can be caused by the formation of amino-oxides, it is recommended that both during the transamidation and during the pyrolysis work is carried out in an inert gas, for example, nitrogen. Amino-oxides display are inclined to undergo the Cope decomposition, which leads to an additional double bond in the molecule, and this acts as a cross-linking site in the subsequent polymerisation, so that water soluble polymers are not formed.

The transamidation reaction is best conducted at temperatures in the range of 100° to 180° C., preferably 130° to 170° C.

The N-substituted$\beta$-saturated propionamides are decomposed pyrolytically in a vacuum of 10 to 100 hPa at temperatures of at least 150, preferably 150° to 300° C., in which connection the preferred pyrolysis temperature will conform to the type of the N-substituted $\alpha,\beta$-unsaturated carboxylic acid amide. It is preferred that the pyrolysis temperature be at 170° to 210° C. In this temperature range N-(',N'-dimethyl-3-aminopropyl)acryl amide or N-(N',N',2,2-tetramethyl-3-aminopropyl)acryl amide are pyrolytically accessible at a high yield.

In this reaction, too, a polymerisation inhibitor can be added. However, this is not usually necessary.

Should it be necessary to add a polymerisation inhibitor, it is recommended that non-volatile substances such as copper powder or organic or inorganic copper (II) salts be used. It is to be recommended that the fractionation of the product mixture also be carried out in a separator column, in a vacuum. The dimensions of the separator column conform to the type of the polyvalent alcohol and of the N-substituted α,β-unsaturated carboxylic acid amide that is to be produced.

Pyrolysis and fractionation are to be undertaken both in combination and as two separate and sequential process stages. There is no risk of a back reaction between the polyvalent alcohols with the double bond that has been formed, since this reaction does not take place without strong basic catalysis. If amines such as those according to EP0070425 are used as protective groups, the back reaction is a disadvantage and causes a drop in yield, which can be effectively avoided in the process according to the present invention.

The process according to the present invention represents a new, low-loss access amongst other things to N-substituted (meth)-acrylamides that are used as valuable monomers in the production of cationic homo- or copolymers. These homo- or copolymers can be used is various ways.

The examples that follow describe the present invention without restricting the use of the process.

EXAMPLE 1

N-(N',N'-dimethyl-3-aminopropyl) acrylamide (DIMAPA)

186.2 g (3.0 mol) 1,2-ethanediol is heated to 45° to 55° C. and 2 g (0.03 mol) 85% potassium hydroxide is added, as is 213.2 g (3.0 mol) of crystalline acrylamide, which is added portion by portion. After this has dissolved, the mixture is stirred for 3 hours at 50° C. It is then neutralized with 6.5 g (0.09 mol) acrylic acid and 460 g (4.5 mol) N,N-dimethylpropane diamine-1,3 is added and heated during the throughput of nitrogen through a temperature interval of 130° to 170° C. for 6-8 hours until the end of ammonia development. The product of the reaction is fed en masse into a column that is heated to 200° to 210° C., when DIMAPA is drawn off to one side through a column at 30 hPa, and the separated 1,2-ethanediol and the excess amine is extracted at the head. The DIMAPA fraction results in 428 g of a 93% product with Kp 30=140° to 150° C., which corresponds to a yield of 85% of the theoretical.

NMR (CD Cl$_3$): δ=1.55 to 1.95 (m,2); 2.25 (s,6); 2.4 (t,2); 3.1 to 3.55 (m,2); 5.45 to 6.3 (m,3); 8.1 (m,1).

EXAMPLE 2

N-(N',N'-2,2-tetramethyl-3-aminopropyl) acrylamide (TEMAPA)

186.2 g (3.0 mol) 1,2-ethanediol is heated to 45° to 55° C. and 2 g (0.03 mol) 85% potassium hydroxide is added, as is 213.2 g (3.0 mol) of crystalline acrylamide, which is added portion by portion. After this has dissolved, the mixture is stirred for 3 hours at 50° C. It is then neutralized with 6 g (0.1 mol) crystalline acetic acid and 586 g (4.5 mol) N,N,2,2-tetramethyl-propanediamine-1,3 is added while stirring and heated for 6 to 8 hours through a temperature range from 130° to 170° C. until ammonia develoment ceases. The product of the reaction is fed en masse into a column that is heated to 190° to 210° C., when TEMAPA is drawn off to one side through a column at 30 hPa, and the separated 1.2-ethandiol and the excess amine is extracted at the head. The TEMAPA fraction results in 523.7 g of a 95% product with Kp 30=135° to 145° C., which corresponds to a yield of 90% of the theoretical.

NMR (CD Cl$_3$): δ=0.9 (s,6); 2.3 (m,8); 3.15 (d,2); 5.3 to 6.5 (m,3); 8.0 (m,1).

EXAMPLE 3

N-(N',N'-dimethyl-3-aminoethyl) acrylamide (DIMETA)

186.2 g (3.0 mol) 1,2-ethanediol is heated to 45° to 55° C. and 2 g (0.03 mol) 85% potassium hydroxide is added, as is 213.2 g (3.0 mol) of crystalline acrylamide, which is added portion by portion. After this has dissolved, the mixture is stirred for 3 hours at 50° C. It is then neutralized with 6.5 g (0.09 mol) acrylic acid and 397 g (4.5 mol) N,N-dimethylethane diamine-1,2 is added and heated during the throughput of nitrogen through a temperature interval of 125° to 170° C. for 6-8 hours until the end of ammonia development. The product of the reaction is fed en masse into a column that is heated to 200° to 210° C., when DIMETA is drawn off to one side through a column at 30 hPa, and the separated 1,2-ethanediol and the excess amine is extracted at the head. The DIMETA fraction results in 409 g of a 95% product with Kp 30=138° to 146° C., which corresponds to a yield of 91% of the theoretical.

NMR (CD Cl$_3$): δ=2.23 (s,6); 2.45 (t,2); 3.3 (m,2); 5.4 to 6.25 (m,3); 7.6 (m,1).

EXAMPLE 4

N-(2-ethylhexyl)-acrylamide 186.2 g (3.0 mol) 1,2-ethanediol is heated to 45° to 55° C. and 2 g (0.03 mol) 85% potassium hydroxide is added, as is 213.2 g (3.0 mol) of crystalline acrylamide, which is added portion by portion. After this has dissolved, the mixture is stirred for 3 hours at 50° C. It is then neutralized with 6.5 g (0.09 mol) acrylic acid and 582 g (4.5 mol) 2-ethylhexylamine is added and heated during the throughput of nitrogen through a temperature interval of 130° to 170° C. for 6-8 hours until the end of ammonia development. The product of the reaction is fed en masse into a column that is heated to 190° to 220° C., when N-(2-ethylhexyl)-acrylamide is drawn off to one side through a column at 30 hPa, and the separated 1,2-ethanediol and the excess amine is extracted at the head. 542 g N-(2-ethylhexyl)-acrylamide (Kp 30=155° to 160° C.) at 95% purity is obtained.

EXAMPLE 5

N-propylacrylamide 186.2 g (3.0 mol) 1,2-ethanediol is heated to 45° to 55° C. and 2 g (0.03 mol) 85% potassium hydroxide is added, as is 213.2 g (3.0 mol) of crystalline acrylamide, which is added portion by portion. After this has dissolved, the mixture is stirred for 3 hours a 50° C. It is then neutralized with 6.5 g (0.09 mol) acrylic acid and 266 g (4.5 mol) n-propylamine is added and heated in an autoclave at an overpressure of 1 bar through a temperature interval of 130° to 170° C. for 6-8 hours. The product of the reaction is fed en masse into a column that is heated to 180° to 200° C., when N-propylacrylamide is drawn off to one side through a column at 66.5 hPa, and the separated 1,2-ethanediol and the excess amine is extracted at the head. 351 g N-propylacrylamide (Kp 66.5=138° to 142° C. is obtained with 4% 1,2-ethandiol as a secondary ingrdient.

EXAMPLE 6

N-(N',N'-dimethyl-3-aminopropyl) acrylamide (DIMAPA)

276.3 g (3.0 mol) glycerine is heated to 55° to 65° C. and 4 g (0.06 mol) 85% potassium hydroxide is added, as is 213.2 g (3.0 mol) of crystalline acrylamide, which is added portion by portion. After this has dissolved, the mixture is stirred for 5 hours at 60° C., when the monomer content has been reduced to 0.8%. 14.5 g (0.2 mol) acrylic acid and 460 g (4.5 mol) N,N-dimethylpropane diamine-1,3 is added and heated during the throughput of nitrogen through a temperature interval of 130° to 170° C. for 8–10 hours until the end of ammonia development. The product of the reaction is fed en masse into a column that is heated to 190° to 210° C., when DIMAPA and glycerine are drawn off to one side through a column at 30 hPa, and the excess amine is extracted at the head. 645 g of a product containing 58% DIMAPA with $Kp_{30}=160°$ to 170° C., is obtained, which corresponds to a yield of 80% of the theoretical.

We claim:

1. A process for the production of N-substituted α, β-unsaturated carboxylic acid amides by the conversion of an unsaturated carboxylic acid amide that is unsubstituted at the amido nitrogen, during basic catalysis in accordance with the Michael addition with an alcohol, transamidation of the resulting Michael adduct with a primary or secondary amine during elimination of the ammonia to form N-substituted carboxylic acid amide with a protected double bond, and with subsequent pyrolytic separation of the alcohol, characterized in that the Michael addition is completed with an organic polyhydroxy compound containing at least two alcoholic OH-groups, this having a boiling point of $>/=150°$ C. at 1010 hPa in a molar ration of 0.75::1 to 2:1, relative to the α,β-unsaturated carboxylic acid amide.

2. A process according to claim 1, characterized in that the molar ratio is 1:1.

3. A process according to claim 1, characterized in that aliphatic straight or branched polyvalent alcohols optionally containing heteroatoms are used as polyhydroxy compounds.

4. A process according to claim 1, characterized in that aliphatic diols with 2 to 6 atoms, aliphatic triols with 3 to 6 carbon atoms, polyvalent alcohols containing ether groups and/or polyvalent aminoalcohols are used.

5. A process according to claim 1, characterized in that the Michael addition is carried out in a temperature range from 20° to 70° C.

6. A process according to claim 1, characterized in that α,β-unsaturated carboxylic acid amides of the general formula

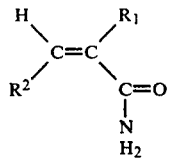

are used in the Michael addition, wherein $R_1$ and $R_2$ stand for hydrogen or methyl.

7. A process according to claim 1, characterized in that the transamidation is carried out with amines of the formula

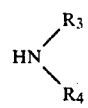

wherein $R_3$ stands for hydrogen and $R_4$ the —Q—$R_5$ radical, in which connection Q stands for an organic radical consisting of an organic radical that is straight or branched, or consisting of 5 or 6 element iso- or heterocyclic rings, or containing such rings, this radical having 2–18 carbon atoms, and $R_3$ and $R_4$ being capable, also in conjunction, of forming a 5- or 6-element iso- or heterocyclic ring, $R_5$ standing for hydrogen, a dialkylamino or alkoxy group, the alkyl radical of which contain in each instance 1 to 4 carbon atoms.

8. A process according to claim 1, characterized in that the transamidation is completed in the presence of catalytic quantities of a carboxylic acid.

9. A process according to claim 1, characterized in that the transamidation is completed at temperatures in the range of 100° to 180° C.

10. A process according to claim 1, characterized in that the pyrolysis of the reamidised Michael adduct is carried out at temperatures of at least 150° C.

11. A process according to claim 1, characterized in that the transamidation and the pyrolysis are carried out in an inert gas.

12. A process according to claims 1 to 11, characterized in that the pyrolysis is carried out in a vacuum and fractionation is also carried out in a vacuum.

13. A process according to claim 1, wherein the organic polyhydroxy compound is at least one member selected from the group consisting of 1,2-ethanediol, glycerine, trimethylolpropane, di-(2-hydroxyethyl)-ether and triethanolamine.

14. A process according to claim 1, characterized in that the Michael addition is carried out in a temperature range from 40° to 50° C.

15. A process according to claim 1, characterized in that the transamidation is completed in the presense of catalytic quantities of acrylic acid.

16. A process according to claim 1, characterized in that the pyrolysis of the reamidised Michael adduct is carried out at a temperature of 150°–300° C.

* * * * *